United States Patent [19]

Louvard et al.

[11] Patent Number: 5,188,967
[45] Date of Patent: Feb. 23, 1993

[54] AGENTS FOR THE IN VITRO DIAGNOSIS OF MALIGNANT CELLS ORIGINATING IN THE DIGESTIVE TRACT

[75] Inventors: Daniel Louvard, Sceaux; Brigitte Dudouet, Paris; Sylvie Robine, Vanves; Monique Arpin, Paris; Eric Pringault, Paris; Alphonse Garcia, Paris, all of France

[73] Assignees: Institut Pasteur; Centre National de la Recherche Scientifique; Institut National de la Sante et de la Recherche Medicale, all of Paris, France

[21] Appl. No.: 662,992

[22] Filed: Feb. 28, 1991

Related U.S. Application Data

[60] Division of Ser. No. 529,676, May 30, 1990, abandoned, which is a continuation of Ser. No. 287,658, Dec. 21, 1988, abandoned, which is a continuation of Ser. No. 6,717, Feb. 19, 1987, abandoned.

[30] Foreign Application Priority Data

May 2, 1985 [FR] France .................................. 85 06707
Nov. 13, 1985 [FR] France .................................. 85 16820

[51] Int. Cl.$^5$ ........................................ G01N 33/574
[52] U.S. Cl. ................................... 436/501; 436/548; 436/813; 435/7.23
[58] Field of Search ...................... 435/95, 110, 172.2, 435/240, 23, 935, 48, 7.23; 436/501, 548, 813

[56] References Cited

U.S. PATENT DOCUMENTS

| | | | |
|---|---|---|---|
| 4,584,268 | 4/1986 | Ceriani et al. | 435/7 |
| 4,666,845 | 5/1987 | Mattes et al. | 435/172.2 |
| 4,687,734 | 8/1987 | Chester | 436/813 |
| 4,708,930 | 11/1987 | Kortright et al. | 435/7 |
| 4,725,538 | 2/1988 | Senger | 435/29 |

OTHER PUBLICATIONS

Alberts et al., Molecular Biology of The Cell, 1983, p. 591 lines 6–7.

*Primary Examiner*—James C. Housel
*Assistant Examiner*—Lyle A. Alexander
*Attorney, Agent, or Firm*—Finnegan, Henderson, Farabow, Garrett & Dunner

[57] ABSTRACT

In vitro diagnosis of malignant cells originating in the digestive tract by placing a biological specimen in contact with a reagent recognizing the gene coding for human villin.

6 Claims, No Drawings

AGENTS FOR THE IN VITRO DIAGNOSIS OF MALIGNANT CELLS ORIGINATING IN THE DIGESTIVE TRACT

This application is a divisional of Ser. No. 07/529,676 filed May 30, 1990 now abandoned which is a continuation of Ser. No. 07/287,658 filed Dec. 21, 1988 now abandoned which is a continuation of Ser. No. 07/006,717 filed Feb. 19, 1987 now abandoned.

The invention is related to agents for the in vitro diagnosis of the existence in man of proliferations of malignant cells derived from tumour cells of the digestive tract, more particularly of the adenocarcinoma type. The agents refer to both in vitro diagnostic procedures and the materials used to implement them, more especially fragments of DNA to be used as probes or even antibodies, preferably monoclonal, directed against human villin.

The invention also covers various applications of such monoclonal antibodies, for example, the purification of human villin from cell extracts containing it. In this sense, the invention also relates to purified villin itself.

It has already been suggested that the detection of structural proteins as specific markers be employed as a means to identify certain types of cells in higher eucaryotes and for monitoring the various stages of their development, particularly in the course of differentiation. Examples of known markers which may be mentioned are the proteins of filaments, such as vimentin, keratins or proteins of neurofilaments which have enabled certain types of cells to be identified and their development to be studied from the stage of embryogenesis to the final stage of cellular differentiation, as well as in relation to their environment (E. LAZARIDES, Nature, 283, 249 (1980) and R. MOLL et al., Cell 31,11 (1982).

The keratins are often considered to be particularly effective markers since they allow a distinction to be made between epithelial and non-epithelial cells. This being said, it has been found that this type of distinction does not always allow the origin of the epithelial cells in question to be unambiguously established.

However, the need to establish the origin of certain types of cells with certainty assumes particular importance in a large number of cases as, for instance, when examination of a biological specimen has provided evidence of tumour cell proliferation, it is necessary to identify the primary tumour cells responsible for the proliferation or it is necessary to detect the existence of metastases which might originate from a cancer of the digestive region or to verify the efficacy of a chemotherapeutic or other type of treatment of metastases. It is well known that the efficacy of an anticancer treatment is dependent on a precise identification of the tumour cells which are the primary cause of the disease.

These comments apply with particular force to the detection, preferably early, of proliferations of tumour cells of digestive (responsible for a considerable proportion of cancers observed in the clinic) or renal origin, or of cells derived from them, more particularly to the identification of characteristic markers of these cells.

Thus, the invention relates more particularly to the detection of tumour cells which have preserved some of the essential phenotypes of the epithelial cells usually present in the mucous membranes of the digestive apparatus, more especially in the intestinal mucosa, and the principal differentiated types of which are composed of absorbant cells, or enterocysts.

More particularly still the invention relates to specific markers capable of being detected, whether or not they are carried by tumour cells.

In particular, an aim of the invention is to make it possible to detect such markers, even when they have become detached from the said tumour cells, in particular as a result of cell necrosis, and released, for example, in to the general circulation.

The marker involved in the context of the present invention is made up of all or part of the villin molecule. The latter is a protein with a molecular weight of about 95,000 daltons and is normally present in the villi of the digestive mucosa, more especially in intestinal villi. Villin is able to bind to actin in the presence of calcium ions.

Although its amino acid sequence may differ slightly from one species to another, the functional characteristics are maintained intact. The techniques of purification presently available have led to chicken and porcine villins being obtained in an essentially pure state. On the other hand, it has not been possible to obtain purified human villin by these techniques.

One of the best known of the villins is that obtained from chicken. It consists of a sequence of 854 amino acids. Proteolysis by trypsin and V-8 protease leads to cleavage at specific sites with the production of 44 Kd, 51 Kd and 10 Kd fragments, the relative positions of which in the villin molecule have been established by Paul MADSUDAIRA, MRC, Laboratory of Molecular Biology, Cambridge, U.K. and John GLENNEY et al., J.B.C., 1981, 256, 8156-8161, to be the following:

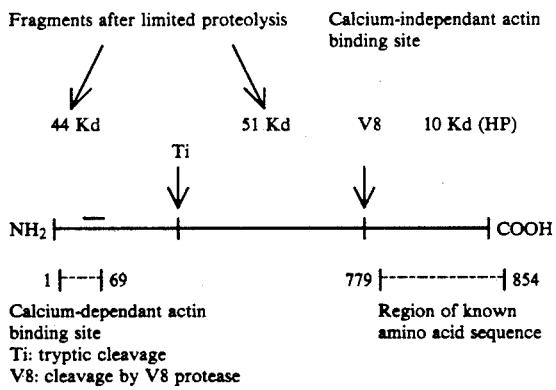

The amino acid sequence of the COOH terminal part of the molecule (779-854) or head piece (or HP peptide) of chicken villin is as follows:

```
                                                    10    11
        Val—Phe—Thr—Ala—Thr—Thr—Thr—Leu—Val—Pro—Thr—Lys—Leu—Glu—

20
        Thr—Phe—Pro—Leu—Asp—Val—Leu—Val—Asn—Thr—Ala—Ala—Glu—Asp—

30   31                                    40    41
        Leu—Pro—Arg—Gly—Val—Asp—Pro—Ser—Arg—Lys—Glu—Asn—His—Leu—
```

-continued

Ser—Asp—Glu—Asn—Phe—Lys—Ala—Val—Phe—Gly—Met—Thr—Arg—Ser—
5051

Ala—Asn—Leu—Pro—Leu—Trp—Lys—Gln—Gln—Asn—Leu—Lys—Lys—Glu—
60617071

Glu—Lys—Gly—Leu—Phe

As a general rule, villin is found more especially in brush borders which are observed on the surface of enterocysts, particularly after they have attained their final stage of differentiation, at the level of the walls of the intestinal lumen. The villi are organelles assembled at the final stage of differentiation of the enterocyst. Villin is localised particularly in the bundles of axial microfilaments of such villi. It contributes to the structure of their cytoskeleton. On examining frozen sections by immunofluorescence, it has been observed that villin is present at the apical pole of elongated cells forming columns at the surface of the internal wall of the intestine, and also close to cells of the proximal tubules of the kidney. In both cases these regions are contiguous with the brush border of the cells concerned. However, villin has not been detected in various other types of villi of various other epithelial cells when the villi were not provided with a well-organised brush border (A. BRETSCHER et al., Exp. Cell Res., 135, 213 (1981) or the article by H. REGGIO et al., published in the monograph entitled "Membranes in Growth and Development" by A. LISS, New York (1982) pp. 89–105).

Furthermore, it has been observed that villin is present in enterocysts from an early stage of their development, well before the organisation of the brush border.

The invention is the consequence of a double discovery. Villin can almost always be detected throughout the course of tumorogenesis of the tissues of the digestive tract, and particularly in cancers of the colon, one of the most widespread forms of cancer, and also in certain types of renal cancer, whereas villin has never been detected in primary tumour cells derived from cancers localised in the tissues of other organs (liver, ovaries, lungs etc.).

Moreover, villin can be detected in vivo at all stages of the development of tumour cells in the digestive region, at both an early and later stages of tumorogenesis, irrespective of the state of differentiation of the cells concerned.

The diagnostic procedure according to the invention, the aim of which, essentially, is the in vitro detection in a biological specimen of tumour cells originating from the digestive region and/or derivatives of them, is characterised in that this biological specimen is placed in contact with reagents exhibiting a specific affinity for villin or recognizing the gene coding for this protein.

The diagnostic procedure according to the invention is applicable to any biological specimen likely to contain tumour cells of digestive origin or tumour cells formed elsewhere in the organism under the influence of primary cells of digestive or renal origin, or even to any biological specimen likely to contain degradation products of these various tumour cells, including the villin marker, produced by necrosis of the cells. This biological specimen may be made up of all types of specimens: fragments of tissue or of solid tumours obtained, for instance, at biopsy, or liquid specimens, particularly whole blood or serum, likely to serve as a vehicle for malignant cells or fragments derived from them.

According to one embodiment of the invention, the reagent used in the diagnostic procedure of the invention is composed of DNA, the sequence of which contains a region coding for an amino acid sequence of human villin, more particularly the COOH-terminal part.

According to another embodiment of the invention, the techniques employed in the diagnostic procedure makes use of immunological methods, the reagent exhibiting a specific affinity for villin being composed of antibodies capable of recognizing villin.

Once bound to villin or to tissues containing it, these antibodies, in turn, are labelled by any known technique or are recognizable by labelled immunoglobulins or other labelled proteins (for example, the A protein of *Staphylococcus aureus*).

Particularly appropriate techniques are those which have been employed in the assays described later and which have led to observations set out above.

The aim of the invention is also to provide new specific agents to detect villin in the villi of enterocysts of similar cells (it is understood that the use of these new agents is not necessarily limited to the employment of the diagnostic procedure according to the invention).

According to one aspect of the invention, these agents are composed of the DNA corresponding to the complete mRNA sequence of human villin or of a DNA fragment, the nucleotide sequence of which contains a region coding for a sequence of amino acids found in human villin, capable of hybridising specifically with a nucleotide sequence coding for villin.

The invention relates more particularly to the use in the above procedure of a DNA corresponding to the complete mRNA of human villin or of a fragment of cDNA characterised by the fact that it contains at least part of the nucleotide sequence coding for the corresponding amino acid sequence of the COOH-terminal of human villin. The nucleotide sequence and the amino acid sequence for which it codes are given below:

```
LYS TRP SER ASN THR LYS SER TYR GLU ASP LEU LYS ALA GLU
AAG TGG AGT AAC ACC AAA TCC TAT GAG GAC CTG AAG GCG GAG

SER GLY ASN SER ARG ASP TRP SER GLN ILE THR ALA GLU VAL
TCT GGC AAC TCT AGG GAC TGG AGC CAG ATC ACT GCT GAG GTC

THR SER PRO LYS VAL ASP VAL PHE ASN ALA ASN SER ASN LEU
ACA AGC CCC AAA GTG GAC GTG TTC AAT GCT AAC AGC AAC CTC
```

```
-continued
SER SER GLY PRO LEU PRO ILE PHE PRO LEU GLU GLN LEU VAL
AGT TCT GGG CCT CTG CCC ATC TTC CCC CTG GAG CAG CTA GTG ASN LYS PRO VAL GLU GLU LEU PRO GLU GLY VAL ASP PRO SER
AAC AAG CCT GTA GAG GAG CTC CCC GAG GGT GTG GAC CCC AGC ARG LYS GLU GLU HIS LEU SER ILE GLU ASP PHE THR GLN ALA
AGG AAG GAG GAA CAC CTG TCC ATT GAA GAT TTC ACT CAG GCC PHE GLY MET THR PRO ALA ALA PHE SER ALA LEU PRO ARG TRP
TIT GGG ATG ACT CCA GCT GCC TTC TCT GCT CTG CCT CGA TGG LYS GLN GLN ASN LEU LYS LYS GLU LYS GLY LEU PHE *
AAG CAA CAA AAC CTC AAG AAA GAA AAG GGA CTA TTT TGA GAAG
AGTAGCTGTGGTTGTAAAGCAGTACCCTACCCTGATTGTAGGGTCTCATTTTCTCA
CCGATATTAGTCCTACACCAATTGAAGTGAAATTTTGCAGATGTGCCTATGAGCAC
AAACTTCTGTGGCAAATGCCAGTTTTGTTTAATAAATGTACCTATTCCTTCAGAAA
GATGATACCCCAAAAAAAAAAAA
```

The nucleotide sequence concerned is used as a probe for the detection of mRNAs or DNAs coding for human villin.

A probe appropriate for this type of detection is advantageously labelled with a radioactive element or any other grouping permitting it to be recognised after hybridisation with the preparation containing the mRNA or DNA to be studied.

Following standard techniques, these probes are placed in contact with biological specimen containing the cells under investigation or directly with their nucleic acids under conditions which allow hybridisation to occur between the nucleotide sequence of the probe any complementary sequence contained in the sample tested.

The reproducibility of detection was tested using a probe containing an insert of 200 base pairs.

These nucleotide probes, which constitute new products forming part of the invention, are also used, according to another aspect, to study the expression of villin mRNAs at each stage of differentiation of the enterocysts and/or cells expressing villin, and in the various stages of maturation of renal or intestinal cells.

The probes thus prepared make it possible to determine the number, organisation and structure of the gene(s) coding for villin starting from a human gene bank.

In conformity with the invention, the nucleotide sequence coding for the terminal portion of human villin is isolated by means of the following procedure:

total mRNA (messenger RNAs) is prepared according to known techniques from a cell line expressing villin a cDNA (complementary DNA) bank is constructed;

these cDNAs are inserted into a vector capable of expressing the protein coded by the insert;

by means of the recombinant vectors obtained a bacterial strain is transformed, then conditions permitting the expression of the desired protein in the bacteria are established;

the recombinant clones containing the clone specific for villin is selected by means of antibodies recognizing villin.

The step leading to the setting up of the cDNA bank is carried out by means of a vector capable of expressing the protein encoded in the inserted cDNA.

Plasmids of the type pEX are particularly advantageous cloning vectors, especially on account of their high yield of expression. Such plasmids have been described by Stanley and Luzio in EMBO Journal, 1984, 3, 1429-1434. They describe plasmids containing the cro-lacZ gene fusion, the expression of which is under the control of the promoter $P_R$ of the bacteriophage lambda. Its expression is temperature-inducible.

A polynucleotide containing several uniques restriction sites is inserted in each of the three possible reading frames, as well as the signals for termination of transcription and translation. The cDNAs inserted at the unique restriction sites are expressed with great efficiency as protein in the form of corresponding hybrid cro-$\beta$gal peptide. The poor solubility of this protein hybrid advantageously reduces the risks of proteolysis in the bacterium and facilitates its immunological detection by specific antibodies.

In order to obtain expression of the corresponding polypeptide in the bacteria a protocol for the sequential addition of different linkers to the two ends of the cDNA according to the technique of Helfmann et al. in P.N.A.S. USA, 1983, 80, 31-35 is employed in order to ensure that the cDNA is inserted in the correct orientation with respect to the cro-lacZ gene. The linkers used correspond to the BamHI and SalI cleavage sites.

These recombinant plasmids are used to transform the bacterial strain employed, according to standard techniques, so that the protein of the desired sequence can be expressed.

Strains of E. coli bacterial are particularly preferred, most especially the strain E. coli pop 2135 which contains the allele cIts857 of the cro repressor.

A bacterial strain is thus obtained containing a cDNA bank corresponding to the mRNA of the cells expressing a high level of villin, containing about 30,000 recombinant clones.

The expression of the protein hybrid is temperature-inducible. Thus, a working temperature is chosen at which the cro gene repressor is inactive. For this purpose, it suffices to incubate the strains for 2 hours at a temperature higher than room temperature, in particular at about 40°-42° C.

The clones recovered after lysis of the bacteria and renaturation of the proteins according to standard techniques are selected by immunological screening.

In a preferred manner, screening of the cDNA bank is first carried out by at least one type of polyclonal anti-villin antibody. The clones reacting specifically with the polyclonal antibody or antibodies are re-screened by means of at least one type of monoclonal antibody directed against epitopes of the COOH-terminus.

Satisfactory screening is achieved by means of a polyclonal anti-villin antibody such as a polyclonal antibody directed against intact porcine villin, followed by one or more monoclonal antibodies recognizing epitopes located in the COOH-terminal region of the molecule.

Screening with a polyclonal antibody is advantageously followed by a secondary screening with another polyclonal antibody, in particular a polyclonal antibody directed against the COOH-terminal fragment of chicken villin.

The invention relates more particularly to a clone carrying a cDNA corresponding to human villin, characterised in that it reacts specifically with a polyclonal antibody directed against intact villin, with a polyclonal antibody directed against the COOH-terminal peptide of chicken villin and with two monoclonal antibodies directed against COOH-terminal epitopes.

The invention also relates to a clone bearing a cDNA corresponding to villin comprising an insert with a poly A sequence and a poly-adenylation site.

According to another aspect of the invention, the agents implemented for the detection of villin consist of monoclonal antibodies.

This aspect of the invention is based on the fact that villins from several species possess common epitopes, accessible to monoclonal antibodies recognizing specifically not only the particular villin used to immunise the animal, the spleen cells of which were fused with appropriate myeloma cells for the production of hybridomas secreting the desired monoclonal antibodies, but also recognizing specifically villins of other species, including human villin.

A preferred monoclonal antibody according to the invention is thus characterised by the following properties:

It recognises purified porcine villin (Western Blotting).

It recognises chicken villin (Western Blotting).

It recognises villin extracted from a cell line derived from an adenocarcinoma of human colon: HT29 (Western Blotting).

It recognises rat villin in immunocytochemistry (cryostat sections of intestinal mucosa of the rat fixed with formaldehyde).

A preferred monoclonal antibody among those satisfying the preceding definition also recognises an epitope contained in the "HP peptide" of chicken villin, recognition being manifest by both the isolated peptide and by the 51 Kd peptide still containing the HP peptide; this antibody does not recognise either the 44 Kd peptide nor the 44 Kd portion of chicken villin.

Moreover, the preferred antibody of the invention recognises the HP protein both in the denatured state, in particular after treatment with sodium dodecyl sulfate (SDS), and in epithelial cells containing villin. This result demonstrates that the epitope carried by the HP peptide is not masked by other proteins in the cellular environment.

The invention obviously also relates to the hybridomas secreting these monoclonal antibodies. An advantageous technique for the preparation of these hybridomas, in particular by fusion of spleen cells of mice immunised against purified porcine villin, on the one hand, with cells of an appropriate myeloma, will be described later. The preferred hybridoma thus obtained (strain BD-D2C3) has been deposited in the Collection Nationale des Cultures de Micro-organismes (CNCM) at the Pasteur Institute, Paris under No. I-440, on Apr. 29th 1985.

According to an advantageous aspect of the invention, the immunogen used to prepare the antibodies can be expressed in the bacterium in large quantities. This immunogen is represented by the peptide encoded in the nucleotide sequence defined above corresponding to the DNA of human villin or a fragment of it.

Following standard techniques, the peptide is injected into animals, the antisera are recovered and, if required, the antibodies are isolated from the antisera by, for example, affinity chromatography. The production of antibodies according to that variant assumes a greater significance in that the HP region encoded in the cDNA fragment defined above is both the most potent immunogen and the most specific region of villin.

It will be noted that the protein encoded in the nucleotide sequence of the villin complemenatry DNA or a fragment of this DNA also represent a source of antigens enabling competitive radioimmunoassays to be carried out (either by the direct ELISA method or by the competitive ELISA method).

However, it is obvious that any other immunogen containing the same immunogenic sequence can be used; for example, the HP peptide itself, grafted on to a carrier molecule such as bovine serum albumin beforehand if necessary, in order to augment its immunogenic properties.

It will be clear to the specialist that, having on hand the preferred monoclonal antibody according to the invention, it is even possible to define the characteristic epitopic region of the HP peptide. In order to identify it more precisely, it would be necessary to use a procedure comprising the following steps:

synthesis of a polynucleotide coding for the HP peptide (or for the part of the HP peptide which may be reasonably considered to contain the desired epitope), linearisation of the plasmid defined above containing the nucleotide sequence coding for the COOH-terminus of villin, and at a restriction site located outside of this sequence, trimming of the linearised plasmid in a controlled manner with an exonuclease, such as Bal 31, religation of the plasmid by means of a DNA ligase, transformation of an appropriate micro-organism, transformable by the corresponding plasmid and capable of expressing the insert contained in the latter, placing of the products expressed by this microorganism in contact again with the antibody under consideration.

the cycle of operations just described being repeated until the immunogenic peptide can no longer be detected in the products expressed in the transformed micro-organism by the religated plasmid.

At the end of each of the cycles of the procedure described above, in particular by sequencing the ends of the plasmid before and after the trimming operation which leads to the loss of the religated plasmid's capacity of recognition, it is possible to locate the epitope at the level of the peptide encoded by the nucleotide sequence eliminated during the last trimming operation. That is to say that the fact that the specialist has at his disposal the monoclonal antibody indicated above is equivalent to his possessing the chemically defined peptide sequence and containing that epitope.

The invention also relates to human villin, practically pure from a biological standpoint, reacting with the preferred monoclonal antibody defined above and giving essentially only one band on polyacrylamide gel electrophoresis, in particular SDS-PAGE.

In fact, human villin can be extracted from a lysate of human enterocysts, in particular as obtained by treatment of the latter with an aqueous solution containing an appropriate detergent, and purified by means of the above-mentioned monoclonal antibody. A purification procedure of this kind makes use of a monoclonal antibody advantageously immobilised on a solid support, preferably suited to the operations of affinity chromatography. For example, the monoclonal antibody is attached to a three-dimensionally cross-linked agarose network, marketed under the name of SEPHAROSE by the Swedish company PHARMACIA AG, by the cyanogen bromide method.

Thus, the invention relates more particularly to a separation procedure for human villin characterised by the operations consisting of passing a solution of it over an affinity column bearing the above-mentioned monoclonal antibody in order to selectively bind human villin, and then recover it by dissociation of the antigen-antibody complex, either by a glycine-based acid buffer at pH 2-4 or by a methylamine-based basic buffer at pH 11, then of dialysis against an ammonium acetate buffer.

It is obvious that the invention also relates to lower molecular weight polypeptides consisting of fragments of human villin. It will be clear to the specialist that the fragments may be obtained by cleavage of human villin by proteases at specific sites. As examples of such enzymes, mention will be made, in the first place, of trypsin and the V8 protease of *Staphylococcus aureus*, alpha chymotrypsin, mouse submaxillary gland protease, marketed by the Boehringer company, the collagenase from *Vibrio alginolyticus chemovar iophagus*, which specifically recognises the peptides Gly-Pro and Gly-Ala, etc.

It goes without saying that the hybridomas and monoclonal antibodies, species-specific or not, which may be produced starting from human villin or its fragments also form part of the invention.

Other characteristics and advantages of the invention will appear in the description which follows of special conditions, indicated as examples, of detection of human villin, of the production and utilisation in assays of hybridomas and monoclonal antibodies.

A procedure for obtaining a clone bearing a portion of cDNA of human villin is also reported.

EXAMPLE 1

Detection of Human Villin

The expression of villin can be studied at different stages of the proliferation of normal and tumour cells originating in the digestive or renal regions, on the one hand, and in other regions of the organism, on the other. The tissues of the organs concerned are frozen, fixed and prepared under conditions permitting the application of the technique described by BROWN and FARQUHAR, Cell 36, 295 (1984) to give cryostat sections.

Sections 5 $\mu$m thick were obtained at $-25°$ C. and deposited on glass slides coated with polylysine. After being immersed in a buffer solution consisting of a phosphate salt solution containing 0.2% of gelatine (PBS-gelatine), the sections were treated with a solution containing 50 $\mu$l of rabbit anti-villin antiserum diluted 1/800 in PBS-gelatine in order to detect the presence of villin, then incubated for 25 minutes at room temperature in a humid chamber.

The sections were then washed three times for ten minutes in PBS-gelatine.

Rabbit anti-IgG labelled with rhodamine (obtained from the Dutch company Nordic Immunological Laboratories) were then added and the sections were incubated in the presence of these anti-IgG at room temperature for 25 minutes. The sections were then washed thoroughly in PBS-gelatine and mounted for examination under a fluorescence microscope (ZEISS photomicroscope) fitted with a Plan Neofluar oil immersion lens and a series of appropriate filters.

The control tissues or tumour tissues from other sources were treated in the same manner.

The following observations were made:

When the tissues were derived from adenocarcinomas of the colon, 11 of the 12 specimens gave a positive result for the presence of villin. Human tumours originating in other organs such as lymphomas, in particular lymphomas of mesenteric nodules and various types of carcinomas originating in other organs and giving rise or not to metastases of the pancreas and oesophagus, did not express this protein.

Generally speaking, a close correlation was observed between the primary intestinal origin of the tumours examined and the expression of villin. Numerous assays were carried out on tumours of obviously other than intestinal origin and the expression of the protein was revealed to be negative in practically all cases.

It is to be noted that villin was always observed in tissues of intestinal origin, whatever the degree of proliferation of the cells in question.

The preceding assays were carried out with polyclonal antibodies. Much more clear-cut results were obtained with the preferred monoclonal antibody which was left in the custody of the CNCM.

The conditions under which the hybridomas secreting these monoclonal antibodies were isolated will be described later in examples. A preferred mode for the implementation of the conditions under which the presence of villin can be diagnosed in the immunological assays of the ELISA type will also be pointed out.

EXAMPLE 2

Preparation of Monoclonal Antibodies Directed Against Villin

A) Immunisation Protocol 6 to 8 weeks old Balb/C mice

Antigen: purified porcine villin (10 mg/ml) (homogeneous band corresponding to a molecular weight of 95 Kd after electrophoresis in a 10% polyacrylamide gel in the presence of SDS):

10 mM imidazole
75 mM HCl
1 mM EGTA
0.1M DTT
50% glycerol

Protocol:

Day 0: IP injection of 50 $\mu$g of pure villin in a 50/50 emulsion (PBS-complete Freund's adjuvant).

Day 14: IP booster injection of 50 $\mu$g of villin (emulsion PBS-complete Freund's adjuvant).

Day 21: IP booster injection of 50 $\mu$g of villin (emulsion PBS-complete Freund's adjuvant).

Day 28: IM injection of 20 $\mu$g of pure villin in PBS solution.

Day 29: IV injection of 10 $\mu$g of pure villin in PBS solution.

Day 32: Fusion

B) Fusion

I) Parent cells a) Myeloma cells:

Sp2/0-Ag 14 line (8-azaguanine resistant)

Sterile culture in DMEM medium containing 10% FCS.

b) Spleen cells:

Origin: spleen of Balb/C mice hyperimmunised against porcine villin.

II) Procedure for cell fusion according to Köhler G and Milstein C (Continuous culture of fused-cells secreting antibody of predefined specificity, Nature 1975, 256, 495).

Fusion under sterile conditions in DMEM medium without serum, in the presence of a 50% solution of polyethylene glycol (PEG 1,000-Merck 9729) in DMEM medium without serum. After counting of the two parental cell types, the suspension of the myeloma cells in culture is mixed with the suspension of spleen cells in the proportion of 1 to 5.

2'30'' contact.

Action of PEG stopped by dilution with complete DMEM medium.

Final dilution of the cell suspension ($2 \times 10^5$ cells/ml) in the selective HAT-DMEM medium.

Distribution in wells of Costar dishes-24 wells 1 ml/well (COSTAR Tissue Culture Cluster 24, Cat. No. 3524, COSTAR 205 Groadway, Cambridge, Ma. USA).

III) Selection of clones

Clones are identified by their capacity to secrete antibodies directed against purified porcine villin.

C) Method of Selection

I) ELISA test: This test provides a demonstration of monoclonal anti-villin antibodies in the culture supernatants after fusion.

Fixation of antigen on a support (ELISA plaque) Concentration: 5 μg/ml in a 50 mM potassium phosphate buffer, pH 8, overnight at 4° C.

Saturation with PBS-Tween 20-BSA.

Incubation I with undiluted hybridoma supernatant, 3 hours at 4° C.

Incubation II with mouse anti-IgG labelled with beta-galactosidase, 2 hours at 4° C.

All washings between each step are carried out with PBS-0.1% Tween 20.

Substrate O-nitrophenyl-beta-D-galactopyranoside (Sigma N11-27) in 0.1M phosphate buffer, pH 7.0. $10^{-3}$M MgSO$_4$. $2 \times 10^{-3}$M MnSO$_4$. $2 \times 10^{-3}$M magnesium tritriplex, anhydrous (Merck 8409). Reading OD at 414 nm.

The clones selected are those for which the hybridoma supernatants give an OD 10 times higher than the background OD II) Western Blotting according to Burnett, Anal. Biochem. 1981, 112, 195-203

This test enables the clones secreting porcine anti-villin monoclonal antibodies and also recognising human and chicken villin to be selected from among the clones giving a positive ELISA test.

Various steps of the test:

a) Polyacrylamide gel electrophoresis of a cell extract of chicken intestinal mucosa and of a cell extract of the line HT29 (adenocarcinoma of human colon) expressing villin.

b) Electrotransfer of the proteins separated on polyacrylamide gel to nitrocellulose paper.

c) Incubation of nitrocellulose paper to which the cell proteins had been transferred with the hybridoma supernatants previously selected in the ELISA test, overnight at 4° C.

d) Incubation for 1 hour at room temperature with mouse anti-IgG labelled with peroxidase.

e) Substrate:

10 mg of diaminobenzidine tetrahydrochloride 20 ml 0.1M Tris HCl pH 7.6

0.2 ml of 1% H$_2$O$_2$

All washings between each step are carried out with new-born calf serum-PBS-Triton X100.

f) positive reaction: rapid appearance of a brown band (molecular weight 95 Kd) if an antigen-monoclonal antibody reaction has taken place.

D) Cloning of the Hybrids Selected

Method of limited dilutions:

Positive clones are diluted with selective medium so as to give only one cell per well (plate with 96 wells) containing macrophages (origin: 4 week-old Balb/C mice) attached to the bottom of the well.

Addition of conditioned selective medium.

Selection of positive clones according to the methods previously described.

Recloning if necessary.

E) Preparation of Ascites

The clones selected are injected into mice (which had received an injection of "PRISTANE" (Aldrich, 2,6,10,14-tetramethylpentadecane) 4 to 5 days previously).

1 to $2 \times 10^6$ cells injected/mouse.

Recovery, 10 to 15 days later, of the ascitic fluid containing the clonal cells which have proliferated. The concentration of anti-villin monoclonal antibody in the ascitic fluid is higher than 1 mg/ml.

Freezing of the selected clones in DMEM medium containing 10% FCS-5% DMSO.

Storage in liquid nitrogen at −176° C.

Direct ELISA Procedure for Titration of Villin.

Adsorption of purified IgGs from the ascite BD-D$_2$C$_3$ at constant concentration on ELISA plaques.

The antibody was purified by ion exchange chromatography (DEAE-Tris acryl) and on a hydroxyapatite column.

Concentration to be determined.

Incubation for 2 hours at 37° C., then overnight at 4° C.

Washing with PBS/0.1% Tween 20.

Saturation of the plaques

Incubation for 30 minutes in the presence of PBS/0.1% Tween 20/0.4% BSA.

Addition of antigen

Serial dilutions of purified villin of decreasing concentration from 5 μg/ml to 1 or 0.1 ng/ml in the presence of 0.4% BSA.

Incubation for 3 hours at 4° C.

Washings with PBS/0.1% Tween 20.

Addition of purified IgG obtained from a polyclonal rabbit serum directed against villin and coupled to beta-galactosidase.

Incubation for 2 hours at 4° C.

Washings with PBS/0.1% Tween 20.

Detection of beta-galactosidase

Addition of 20 mg of p-nitrophenyl-beta-D-galactopyrannoside from a solution containing 4 mg/ml to 20 ml of 0.1M phosphate buffer, pH 7, $10^{-3}$M MgSO$_4$, $2 \times 10^{-4}$M MnSO$_4$, $2 \times 10^{-3}$M EDTA (Merck 8409)

Incubation for x hours at 37° C.

Optical density reading at 414 nm.

EXAMPLE 3

Clinical Observations.

Measurements have been made of the amounts of villin detectable in the serum by making use of the ELISA test described below, the sensitivity of which makes it possible to detect very low levels of villin in a cell extract (0.5 ng of villin per mg of total protein). In fact, the inventors have confirmed that necrosis of cells containing villin, an intracellular protein expressed by normal and tumor cells of the digestive tract, may lead to its liberation into the circulation under certain physiopathological conditions.

A study conducted on a population of blood donors (n=190) showed that villin was not detectable in the vast majority (n=168) of the sera. However, a detectable concentration of villin was present in the serum of a small number of individuals (n=15) (5 to 10 ng/ml). This value is regarded as a concentration of villin which has no pathological significance. There were also several individuals (n=7) in whom the level of villin was indeed higher than the basal value (50 to 100 ng/ml). The study of these so-called "normal" individuals (3.6%) was not extended to include clinical examination of their digestive tract (fiber optic endoscopy, colonoscopy).

The initial results obtained in different gastro-intestinal diseases are summarized in the table below.

Detection of measurable amounts (values lying between 10 and 10,000 ng/ml) of villin in the sera of patients suffering from:

Malignant diseases of the digestive tract:
colorectal cancers
gastric cancers
Benign diseases of the digestive tract:
villous tumors
Crohn's disease
ulcerative colitis
ulcers of the duodenal, gastric and esophagal bulb.

On the other hand, it is important to note that polyadenomas of the digestive tract ("polyps") do not lead to the liberation of this protein into the circulation.

This study also enabled certain other deductions to be made:

1. There seems to be no correlation between the amount of circulating villin and the size and stage of development of the tumor.
2. Measurement of this protein during the post-operative follow-up showed a fall in its serum concentration after complete surgical excision. On the other hand, in cases in which tumor tissue persisted (incomplete excision, recurrences, metastases), the level of villin was observed to remain stationary or increase.

This study indicated that villin is not usually detectable in the serum of normal subjects, whereas it can be measured in the serum of patients who have contracted malignant diseases (colic or rectal cancers) or who are suffering from benign ulcerations (diseases such as Crohn's disease, ulcerative colitis, ulcers) of the digestive tract which provoke the intervention of necrotic and inflammatory processes of the digestive mucous.

The measurement of the concentration of villin in the blood also proved to be of importance in the surveillance of benign diseases (ulcerations and inflammatory diseases of the digestive tract). Moreover, in the study of circulating villin, it is possible to use the antibodies of the invention in conjunction with other tumoral markers such as CEA (carcinoembryonic antigen), which is presently used for the surveillance of the evolution of cancers but the principal disadvantages of which are: 1/ low specificity for the organ affected; 2/ its presence in various benign diseases.

EXAMPLE 4

Preparation of cDNA Corresponding to Human Villin

Preparation of the mRNAs

The mRNAs are prepared from the HT29 cell line derived from a human colon adenocarcinoma. The RNAs are extracted by the guanidium chloride method described by Ullrich et al. in Science, 1977, 196, 1313-1319. The purification of the poly A+ mRNAs is carried out by chromatography on a column of oligo dT-cellulose according to the method described by Aviv and Leder in Proc. Natl. Acad. Sci. USA, 1972, 69, 1408-1412.

Preparation of cDNAs

The first and second strand of the cDNAs are prepared according to the method of Fiddes and Goodman described in Nature, 1979, 281, 351-355. The sequential addition of the linkers SalI at the 3' end and Bam H1 at the 5' end is carried out by the method of Helfmann et al. reported in Proc. Natl. Acad. Sci. USA, 1983, 80, 31-35.

This leads to a cDNA bank containing about 30,000 recombinant clones.

Vector

Plasmids pEX 1-3 (see Stanley and Luzio, EMBO Journal, 1984, 3, 1429-1430). These vectors derive from plasmids containing the cro-lacZ gene fusion, the expression of which is under the control of the promoter PR of the bacteriophage lambda. A polynucleotide containing several unique restriction sites was inserted at the 3' end of the lacZ gene. The termination signals for transcription and translation are also inserted in the three reading frames.

The cDNAs were inserted in each of the pEX plasmids under the direction of the restriction enzymes Bam H1 and SalI. Thus, they all have the same orientation with respect to the cro-lacZ gene.

Transformation.

The bacterial strain used is *E. coli* pop 2135, constructed by O. Raibaud as described in Nucleic Acid Research in the following manner:

The 2.3 kb fragment BglII of the phage lambda, carrying the C1857 allele and the promoter $P_R$ is cloned into the Bam H1 site of a polylinker as indicated in the following scheme:

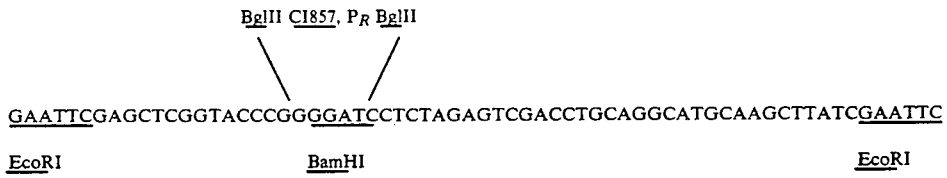

GAATTCGAGCTCGGTACCCGGGGATCCTCTAGAGTCGACCTGCAGGCATGCAAGCTTATCGAATTC

EcoRI            BamHI                                      EcoRI

The EcoRI fragment thus obtained is then cloned into the EcoRI site of pOM41 and transferred into the chromosome of the strain C600 (see Gene, 29, 231–241).

By cotransduction using Pl' with a marker linked to aroB, this structure is introduced into the background MM294 (F⁻ endA thi hsdR). *E. coli* pop 2135 is obtained: orientation maIT, C1857, $P_R$, maIPQ.

The transformation of the bacterial strain *E. coli* pop 2135 by the recombinant plasmids is carried out according to the technique using rubidium described by Hanahan et al., J. Mol. Biol., 1983, 166, 557–580. This strain contains the allele cIts857 of the cro repressor.

The number of recombinants obtained is of the order of $10^3$ to $10^4$ ng of cDNA.

Selection of clones by immunological detection

The recombinant clones obtained are spread on nitrocellulose filters. The synthesis of the hybrid protein is induced during 2 hours of incubation at 42° C. After lysis of the bacteria by SDS and renaturation of the proteins in the absence of methanol, the clones are analysed by immunological screening. Renaturation of the proteins is carried out according to the technique of Burnett reported in Anal. Biochem. 1981, 112, 195–203.

In the first step, the bank is screened by a polyclonal antibody directed against intact porcine villin. A secondary screening is then carried out using a polyclonal antibody directed against a COOH-terminal fragment of chicken villin and two monoclonal antibodies ($BDD_2C_3$ and $IID_3H_9$) recognizing epitopes located in the COOH-terminal region of the molecule.

The clone pEXZ-V19 contains an insert of 510 base pairs. The coding region represents 310 base pairs. It is followed by non coding sequences of 200 base pairs.

The cloned cDNA codes for the 95 COOH-terminal amino acids of human villin and represents about 1/10 of the total protein (molecular weight: 95 Kd).

REFERENCES (1) Ullrich, A., Shine, J., Chirgwin, J., Pictet, R., Tischer, E., Rutter, W. J. & Goodman, H. M. Rat insulin genes: construction of plasmids containing the coding sequences. Science, 1977, 196, 1313–1319.

(2) Aviv, H. & Leder, P. Purification of biologically active globin mRNA by chromatography on oligothymidylic acid cellulose. Proc. Natl. Acad. Sci. USA, 1972, 69, 1408–1412.

(3) Fiddes, J. C. & Goodman, H. M. Isolation, cloning and sequence analysis of the cDNA for the alphasubunit of human chorionic gonadotropin. Nature, 1979, 281, 351–355.

(4) Helfman, D. M., Feramisco, J. R., Fiddes, J. C., Thomas, G. P. P Hughes, S. H. Identification of clones that encode chicken tropomyosin by direct immunological screening of a cDNA expression library. Proc. Natl. Acad. Sci. USA, 1983, 80, 31–35.

(5) Stanley, K. K. & Luzio, J. P. Construction of a new family of high efficiency bacterial expression vectors: identification of cDNA clones coding for human liver. EMBO Journal, 1984, 3, 1429–1434.

(6) Stanley K. K. Sclubilization and immune-detection of beta-galactosidase hybrid proteins carrying foreign antigenic determinants. Nucleic Acids Res., 1983, 11, 4077–4092.

(7) Hanahan, D. Studies on transformation of *E. coli* with plasmids. J. Mol. Biol., 1983, 166, 557–580.

(8) Burnett, W. N. "Western Blotting": Electrophoretic transfer of proteins from sodium dodecyl sulfatepolyacrylamide gels to unmodified nitrocellulose and radiographic detection with antibody and radioiodinated protein A. Anal. Biochem., 1981, 112, 195–203.

We claim:

1. An in vitro method of detecting a tumor associated with cells of renal or intestinal origin, wherein said method comprises
   (a) contacting a specimen of tissue or serum from a human subject with a reagent comprising detectable anti-villin antibodies, to form villin- anti-villin immune complexes;
   (b) detecting the presence of said immune complexes; and
   (c) on the basis of the presence of said immune complexes, diagnosing the presence or absence of said tumor.

2. An in vitro method of detecting a tumor as claimed in claim 1, wherein said anti-villin antibody is selected from the group consisting of antibodies to human villin, porcine villin, chicken villin, villin from a HT29 cell line, and rat villin.

3. An in vitro method of detecting a tumor as claimed in claim 2, wherein said anti-villin antibody is an anti-human villin antibody.

4. An in vitro method of detecting a tumor as claimed in claim 3, wherein said anti-villin antibody is capable of reacting with the C-terminal portion of human villin that comprises an amino acid sequence:

```
LYS TRP SER ASN THR LYS SER TYR GLU ASP LEU LYS ALA GLU
AAG TGG AGT AAC ACC AAA TCC TAT GAG GAC CTG AAG GCG GAG

SER GLY ASN SER ARG ASP TRP SER GLN ILE THR ALA GLU VAL
TCT GGC AAC TCT AGG GAC TGG AGC CAG ATC ACT GCT GAG GTC

THR SER PRO LYS VAL ASP VAL PHE ASN ALA ASN SER ASN LEU
ACA AGC CCC AAA GTG GAC GTG TTC AAT GCT AAC AGC AAC CTC
```

-continued

```
SER SER GLY PRO LEU PRO ILE PHE PRO LEU GLU GLN LEU VAL
AGT TCT GGG CCT CTG CCC ATC TTC CCC CTG GAG CAG CTA GTG

ASN LYS PRO VAL GLU GLU LEU PRO GLU GLY VAL ASP PRO SER
AAC AAG OCT GTA GAG GAG CTC CCC GAG GGT GTG GAC CCC AGC

ARG LYS GLU GLU HIS LEU SER ILE GLU ASP PHE THR GLN ALA
AGG AAG GAG GAA CAC CTG TOC ATT GAA GAT TTC ACT CAG GCC

PHE GLY MET THR PRO ALA ALA PHE SER ALA LEU PRO ARG TRP
TIT GGG ATG ACT CCA GCT GCC TTC TCT GCT CTG CCT CGA TGG

LYS GLN GLN ASN LEU LYS LYS GLU LYS GLY LEU PHE *
AAG CAA CAA AAC CTC AAG AAA GAA AAA GGA CTA TTT TGA GAAG
AGTAGCTGTGGTTGTAAAGCAGTACCCTACCCTGATTGTAGGGTCTCATTTTCTCA
CCGATATTAGTCCTACACCAATTGAAGTGAAATTTTGCAGATGTGCCTATGAGCAC
AAACTTCTGTGGCAAATGCCAGTTTTGTTTAATAAATGTACCTATTCCTTCAGAAA
GATGATACCCCAAAAAAAAAAAA.
```

5. An in vitro method of detecting a tumor as claimed in claim 2, wherein said anti-villin antibody is an anti-chicken villin antibody.

6. An in vitro method of detecting a tumor as claimed in claim 5, wherein said anti-villin antibody is capable of reacting with the C-terminal portion of chicken villin that comprises an amino acid sequence:

```
 1                                          10  11
Val—Phe—Thr—Ala—Thr—Thr—Thr—Leu—Val—Pro—Thr—Lys—Leu—Glu—

20
Thr—Phe—Pro—Leu—Asp—Val—Leu—Val—Asn—Thr—Ala—Ala—Glu—Asp—

30  31                                     40  41
Leu—Pro—Arg—Gly—Val—Asp—Pro—Ser—Arg—Lys—Glu—Asn—His—Leu—

50  51
Ser—Asp—Glu—Asn—Phe—Lys—Ala—Val—Phe—Gly—Met—Thr—Arg—Ser—

60  61                                     70  71
Ala—Asn—Leu—Pro—Leu—Trp—Lys—Gln—Gln—Asn—Leu—Lys—Lys—Glu—

Glu—Lys—Gly—Leu—Phe.
```

* * * * *